(12) United States Patent
Turner et al.

(10) Patent No.: US 8,312,800 B2
(45) Date of Patent: Nov. 20, 2012

(54) PNEUMATIC SYSTEM FOR A VITRECTOR

(75) Inventors: Denis Turner, Vista, CA (US); Robert Palino, Aliso Viejo, CA (US); Argelio Olivera, Mission Viejo, CA (US); Mark Hopkins, Mission Viejo, CA (US)

(73) Assignee: Novartis AG, Basel (CH)

( * ) Notice: Subject to any disclaimer, the term of this patent is extended or adjusted under 35 U.S.C. 154(b) by 1449 days.

(21) Appl. No.: 11/614,678

(22) Filed: Dec. 21, 2006

(65) Prior Publication Data
US 2008/0149197 A1 Jun. 26, 2008

(51) Int. Cl.
*A61F 9/007* (2006.01)
*E03B 9/00* (2006.01)
(52) U.S. Cl. .......... 83/639.1; 604/22; 606/170; 137/560
(58) Field of Classification Search .................. 83/639.1, 83/53, 370, 364, 902; 606/170, 1; 604/22; 128/200.42; 137/560, 15.14, 81.5; 112/130; 702/50; 451/102, 39; 73/37.7, 37
See application file for complete search history.

(56) References Cited

U.S. PATENT DOCUMENTS

| | | | |
|---|---|---|---|
| 812,162 A | 2/1906 | Bemis | |
| 2,016,746 A | 10/1935 | Ireland | |
| 2,707,389 A | 5/1955 | Fortier | |
| 3,084,674 A | 4/1963 | Watson | |
| 3,646,727 A | 3/1972 | Wachsmuth | |
| 3,703,139 A | 11/1972 | Furlong | |
| 3,726,307 A | 4/1973 | Carman et al. | |
| 3,867,934 A | 2/1975 | Ollivier | |
| 4,075,928 A | 2/1978 | Bitonti | |
| 4,077,567 A | 3/1978 | Ginn et al. | |
| 4,086,804 A | 5/1978 | Ruby | |
| 4,253,480 A | 3/1981 | Kessel et al. | |
| 4,323,064 A | 4/1982 | Hoenig et al. | |
| 4,331,130 A | 5/1982 | Lewicky | |
| 4,344,144 A | 8/1982 | Damico et al. | |
| 4,449,550 A | 5/1984 | Ranalli | |
| 4,476,532 A | 10/1984 | Akiyama et al. | |
| 4,590,935 A | 5/1986 | Ranalli | |

(Continued)

FOREIGN PATENT DOCUMENTS

DE 39 25 405 A1 2/1991

(Continued)

OTHER PUBLICATIONS

Office Action, U.S. Appl. No. 11/554,387, Sep. 17, 2009, 23 pages.

(Continued)

*Primary Examiner* — Ghassem Alie
(74) *Attorney, Agent, or Firm* — Darien Reddick

(57) ABSTRACT

A system for providing pneumatic power to a vitrector includes first and second output ports, an output valve, an isolation valve, and three manifolds. The first and second output ports provide pressurized gas to power a vitrector. The output valve alternately provides pressurized gas to the first and second output ports. The isolation valve provides pressurized gas to the output valve. Two manifolds fluidly connect the output valve to the first and second output ports. A third manifold fluidly connects the isolation valve to the output valve. When the isolation valve provides pressurized gas to the output valve, the output valve operates at a high rate of speed to alternately provide pressurized gas to the first and second output ports thereby powering the vitrector.

18 Claims, 6 Drawing Sheets

U.S. PATENT DOCUMENTS

| | | | |
|---|---|---|---|
| 4,622,503 A | 11/1986 | Sunblom et al. | |
| 4,650,460 A | 3/1987 | Roizenblatt | |
| 4,650,462 A | 3/1987 | Desatnick et al. | |
| 4,679,583 A | 7/1987 | Lucas et al. | |
| 4,706,687 A | 11/1987 | Rogers et al. | |
| 4,757,814 A | 7/1988 | Wang et al. | |
| 4,770,654 A | 9/1988 | Rogers et al. | |
| 4,790,816 A | 12/1988 | Sunblom et al. | |
| 4,810,242 A | 3/1989 | Sundblom et al. | |
| 4,840,111 A | 6/1989 | Garnjost | |
| 4,887,636 A | 12/1989 | Rothen | |
| 4,933,843 A | 6/1990 | Scheller et al. | |
| 5,094,260 A | 3/1992 | Stuart et al. | |
| 5,138,838 A | 8/1992 | Crosser | |
| 5,176,628 A | 1/1993 | Charles et al. | |
| 5,239,861 A | 8/1993 | Fujita et al. | |
| 5,279,322 A | 1/1994 | Nakamura et al. | |
| 5,314,295 A | 5/1994 | Lukkari et al. | |
| 5,318,072 A | 6/1994 | Goedecke | |
| 5,417,246 A | 5/1995 | Perkins et al. | |
| 5,549,139 A | 8/1996 | Perkins et al. | |
| 5,571,248 A | 11/1996 | Seetharaman et al. | |
| 5,580,347 A | 12/1996 | Reimels | |
| 5,587,536 A | 12/1996 | Rasmussen | |
| 5,674,194 A | 10/1997 | Jung et al. | |
| 5,829,335 A | 11/1998 | Ewald et al. | |
| 5,846,257 A | 12/1998 | Hood | |
| 5,857,485 A | 1/1999 | Perkins et al. | |
| 5,979,494 A | 11/1999 | Perkins et al. | |
| 6,065,494 A | 5/2000 | Thomsen et al. | |
| 6,155,233 A | 12/2000 | Wade et al. | |
| 6,155,289 A | 12/2000 | Carlsen et al. | |
| 6,450,966 B1 | 9/2002 | Hanna | |
| 6,474,289 B1 | 11/2002 | Lilly et al. | |
| 6,514,268 B2 | 2/2003 | Finlay et al. | |
| 6,575,990 B1 | 6/2003 | Wang et al. | |
| 6,655,404 B2 | 12/2003 | Hilaire | |
| 6,773,445 B2 | 8/2004 | Finlay et al. | |
| 6,779,541 B2 | 8/2004 | Inayama et al. | |
| 7,089,733 B1 | 8/2006 | Jackson et al. | |
| 7,244,240 B2 | 7/2007 | Nazarifar et al. | |
| 7,335,217 B2 | 2/2008 | Wang et al. | |
| 7,470,277 B2 | 12/2008 | Finlay et al. | |
| 7,814,936 B2 | 10/2010 | Catron | |
| 2002/0069916 A1 | 6/2002 | Ferguson et al. | |
| 2002/0117214 A1 | 8/2002 | Tucker et al. | |
| 2002/0173814 A1 | 11/2002 | Jung et al. | |
| 2002/0174905 A1 | 11/2002 | Latino et al. | |
| 2003/0042182 A1 | 3/2003 | Moscaritolo | |
| 2003/0078609 A1 | 4/2003 | Finlay et al. | |
| 2006/0271082 A1 | 11/2006 | Kirchhevel et al. | |
| 2007/0270735 A1 | 11/2007 | Williams et al. | |
| 2007/0270746 A1 | 11/2007 | King | |
| 2007/0282262 A1 | 12/2007 | Williams et al. | |
| 2008/0082077 A1 | 4/2008 | Williams | |
| 2008/0142093 A1 | 6/2008 | Turner et al. | |
| 2008/0146988 A1 | 6/2008 | Olivera et al. | |
| 2008/0149197 A1 | 6/2008 | Turner et al. | |
| 2008/0168985 A1 | 7/2008 | Turner et al. | |
| 2009/0124962 A1 | 5/2009 | Hopkins et al. | |
| 2009/0203480 A1 | 8/2009 | Petzold et al. | |
| 2009/0259242 A1 | 10/2009 | Gerg et al. | |
| 2009/0270793 A1* | 10/2009 | Domash et al. | 604/22 |

FOREIGN PATENT DOCUMENTS

| | | |
|---|---|---|
| DE | 42 32 586 A1 | 3/1994 |
| DE | 198 21 420 C1 | 10/1999 |
| DE | 10247869 A1 | 5/2004 |
| DE | 10341477 | 3/2005 |
| DE | 20 2005 009670 U1 | 9/2005 |
| DE | 10247869 B4 | 2/2007 |
| EP | 0469641 B1 | 6/1989 |
| EP | 0626628 A1 | 11/1994 |
| EP | 0626628 B1 | 12/1997 |
| EP | 0673475 B1 | 6/1998 |
| EP | 874163 A2 | 10/1998 |
| EP | 0884667 A1 | 12/1998 |
| EP | 1 172 586 A1 | 1/2002 |
| EP | 1660244 B1 | 12/2006 |
| EP | 1734260 | 12/2006 |
| EP | 2032878 | 12/2009 |
| GB | 792397 | 3/1958 |
| GB | 1 213 723 | 11/1970 |
| GB | 2 016 746 A | 9/1979 |
| GB | 2 389 423 A | 12/2003 |
| JP | 61-18133 | 3/1982 |
| JP | 62-203437 | 12/1987 |
| JP | 5-87779 | 1/1989 |
| JP | 2-223846 | 9/1990 |
| JP | 07259801 A | 10/1995 |
| JP | 09225698 A | 9/1997 |
| WO | WO 95/31141 A1 | 11/1995 |
| WO | WO 00/78371 A1 | 12/2000 |
| WO | WO 01/64120 A1 | 9/2001 |
| WO | WO 2008/000599 A1 | 1/2008 |
| WO | WO 2008/054944 A1 | 5/2008 |
| WO | WO 2008/105950 A2 | 9/2008 |
| WO | WO 2008/105950 A3 | 9/2008 |
| WO | 2008140537 A1 | 11/2008 |
| WO | 2008147429 A2 | 12/2008 |
| WO | WO 2008/147429 A2 | 12/2008 |
| WO | WO 2008/147429 A3 | 12/2008 |

OTHER PUBLICATIONS

International Searching Authority, PCT International Preliminary Report on Patentability, PCT/US2007/079915, May 15, 2009, 6 pages.

International Searching Authority, PCT International Preliminary Report on Patentability, PCT/US2007/080265, Sep. 1, 2009, 8 pages.

International Searching Authority, PCT International Preliminary Report on Patentability, PCT/US2007/080540, Jun. 23, 2009, 5 pages.

Office Action, U.S. Appl. No. 11/610,275, Sep. 14, 2009, 18 pages.

International Searching Authority, PCT International Preliminary Report on Patentability, PCT/US2007/080239, Jun. 16, 2009, 8 pages.

Office Action, U.S. Appl. No. 11/610,275, Nov. 25, 2008, 10 pages.

Office Action, U.S. Appl. No. 11/610,275, Apr. 13, 2009, 16 pages.

Kabei, Shimemura, et al., A portable pneumatic driving unit for a left ventricular assist device, Int. J. Artif. Organs, 1988, 186-90, 11(3).

Nachlas, Marvin, et al., A simple portable pneumatic pump for external cardiac massage, The American Journal of Cardiology, 1962, 107-109, 10(1).

J.L. Waldeck; "The Development of a Portable Pressure Source for the Static and Dynamic Calibration of Pressure Transducers"; Journal of Wind Engineering and Industrial Aerodynamics, 1987, 26(2), 213-230.

Ellis, George, et al., Microcomputer-Controlled Precision Pressure Generator, IEEE Transactions on Instrumentation and Measurement, 1977, 214-217, 26(3).

Whalen, R.L., et al., An electromagnetic pneumatic blood pump driver, American Society of Artificial Internal Organs, 1988, 721-725, 34(3).

Turkentine, R.B., et al., Pressure-operated shutter for thin-film monitor, Journal of Physics E: Scientific Instruments, 1979, 12(1).

Rogers, Richard C., An inexpensive picoliter-volume pressure ejection system, Brain Research Bulletin, 1985, 669-671, 15(6).

Johnson, Kenneth S., et al., A submersible flow analysis System, Analytical Chimica Acta, 1986, 245-257, 179.

Tabassum, Alim Abid, Solar refrigeration: evaluation of technical options and design of a solar-generator-adsorber for a novel adsorption refrigerator, Cranfield Univ., 1989.

Buchanan, P.R., et al., Recovery of ventilation distributions by gas wash-out of a mechanical pump, Clinical Physics and Physiological Measurement, 1986, 7(3).

International Search Report for PCT/US2007/080239, Publication No. WO2008/140537, 3 pages.

International Search Report for PCT/US2007/079915, Publication No. WO2008/054944, 2 pages.

International Search Report for PCT/US2007/080265, Publication No. WO2008/105950, 3 pages.

International Search Report for PCT/US2007/080540, Publication No. WO2008/147429, 4 pages.

Document labeled "D1A" titled "oerHi Switzerland" received in an opposition filed Dec. 2, 2011 in the corresponding EP Patent No. EP2099399; Granted Mar. 2, 2011, 4 pages.

Document labeled "D1B" titled "Pneumatik Einheit" received in an opposition filed Dec. 2, 2011 in the corresponding EP Patent No. EP2099399; Granted Mar. 2, 2011, 1 page.

Document labeled "D1C" entitled "OS3 Basic: Pneumatik" received in an opposition filed Dec. 2, 2011 in the corresponding EP Patent No. EP2099399; Granted Mar. 2, 2011, 1 page.

Document labeled "D1D" entitled "SPS Highspeed Vitrektomie Stripper" received in an opposition filed Dec. 2, 2011 in the corresponding EP Patent No. EP2099399; Granted Mar. 2, 2011, 1 page.

Document labeled "D1E" and "D2E" entitled "Oertli Instrumente AG/Alcon Inc.—Eidesstattliche Erklarung" received in an opposition filed Dec. 2, 2011 in the corresponding EP Patent No. EP2099399; Granted Mar. 2, 2011, 8 pages.

English translation of document labeled "D1E" and "D2E" entitled "Oertli Instrumente AG/Alcon Inc.—Affidavit" received in an opposition filed Dec. 2, 2011 in the corresponding EP Patent No. EP2099399; Granted Mar. 2, 2011, 3 pages.

Document labeled "D1F" entitled "Strukturstuckliste" received in an opposition filed Dec. 2, 2011 in the corresponding EP Patent No. EP2099399; Granted Mar. 2, 2011, 2 pages.

Document labeled "D2A" entitled "Kopie" received in an opposition filed Dec. 2, 2011 in the corresponding EP Patent No. EP2099399; Granted Mar. 2, 2011, 5 pages.

Document labeled "D2B" entitled "Oertli Instrumente AG, PN210062d" received in an opposition filed Dec. 2, 2011 in the corresponding EP Patent No. EP2099399; Granted Mar. 2, 2011, 2 pages.

Document labeled "D2C" entitled "OS Basic: Pneumatik; Fast VIT-PN" received in an opposition filed Dec. 2, 2011 in the corresponding EP Patent No. EP2099399; Granted Mar. 2, 2011, 1 page.

Document labeled "D2D" entitled "SPS Highspeed Vitrektomie Stripper" received in an opposition filed Dec. 2, 2011 in the corresponding EP Patent No. EP2099399; Granted Mar. 2, 2011, 1 page.

Document labeled "D2F" entitled "Service Manual, OS3 Basic" received in an opposition filed Dec. 2, 2011 in the corresponding EP Patent No. EP2099399; Granted Mar. 2, 2011, 25 pages.

Document labeled "D2G" entitled "Stuckliste-Pneumatik Einheit" received in an opposition filed Dec. 2, 2011 in the corresponding EP Patent No. EP2099399; Granted Mar. 2, 2011, 2 pages.

Document labeled "D2H" entitled "Stuckliste-Pneumatikeinheit SMC Ventile" received in an opposition filed Dec. 2, 2011 in the corresponding EP Patent No. EP2099399; Granted Mar. 2, 2011, 1 page.

Document labeled "D2I" entitled "Application Note" received in an opposition filed Dec. 2, 2011 in the corresponding EP Patent No. EP2099399; Granted Mar. 2, 2011, 4 pages.

Document labeled "D3" entitled "US Patent No. 5417246" received in an opposition filed in the corresponding EP Patent No. EP2099399; Granted Mar. 2, 2011, 30 pages.

Document labeled "Electronic Receipt" entitled "Empfangsbescheinigung" received in an opposition filed in the corresponding EP Patent No. EP2099399; Granted Mar. 2, 2011, 2 pages.

Document labeled "EP Notice of Opposition—German" entitled "Einspruch gegen ein europaisches Patent" received in an opposition filed Dec. 2, 2011 in the corresponding EP Patent No. EP2099399; Granted Mar. 2, 2011, 5 pages.

English translation of document labeled "Notice of Opposition—German" entitled "Opposition to EP 2099399 of Alcon Inc." received in an opposition filed Dec. 2, 2011 in the corresponding EP Patent No. EP2099399; Granted Mar. 2, 2011, 15 pages.

Document labeled "Notice of Opposition—German" entitled "Isler & Pedrazzini AG" received in an opposition filed Dec. 2, 2011 in the corresponding EP Patent No. EP2099399; Granted Mar. 2, 2011, 18 pages.

* cited by examiner

PNEUMATIC SYSTEM FOR A VITRECTOR

FIELD OF THE INVENTION

The present invention relates to a pneumatic module for a surgical machine and more particularly to a pneumatic module designed to provide power to a vitrector.

BACKGROUND OF THE INVENTION

Vitreo-retinal procedures include a variety of surgical procedures performed to restore, preserve, and enhance vision. Vitreo-retinal procedures are appropriate to treat many serious conditions of the back of the eye. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

The retinal surgeon performs a vitrectomy with a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a controlled fashion. This prevents significant traction on the retina during the removal of the vitreous humor.

The surgical machine used to perform a vitrectomy and other surgeries on the posterior of the eye is very complex. Typically, such an ophthalmic surgical machine includes a main console to which the numerous different tools are attached. The main console provides power to and controls the operation of the attached tools.

The attached tools typically include probes, scissors, forceps, illuminators, vitrectors, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic or air distribution module. This pneumatic module conditions and supplies compressed air or gas to power the tools. Typically, the pneumatic module is connected to a cylinder that contains compressed gas. The pneumatic module must provide the proper gas pressure to operate the attached tools properly.

In particular, one tool, a vitrector, is utilized to cut the vitreous for removal during a vitrectomy. Vitrectors operate at different speeds. Generally, the faster a vitrector operates, the quicker a vitrectomy can be performed. It would be desirable to have a pneumatic module to provide power to a vitrector to enable fast operation thereof with a minimal number of parts.

SUMMARY OF THE INVENTION

In one embodiment consistent with the principles of the present invention, the present invention is a system for providing pneumatic power to a vitrector. The system includes first and second output ports, an output valve, an isolation valve, and three manifolds. The first and second output ports provide pressurized gas to power a vitrector. The output valve alternately provides pressurized gas to the first and second output ports. The isolation valve provides pressurized gas to the output valve. Two manifolds fluidly connect the output valve to the first and second output ports. A third manifold fluidly connects the isolation valve to the output valve. When the isolation valve provides pressurized gas to the output valve, the output valve operates at a high rate of speed to alternately provide pressurized gas to the first and second output ports thereby powering the vitrector.

In another embodiment consistent with the principles of the present invention, the present invention is a system for providing pneumatic power to a vitrector. The system includes first and second output ports, an output valve, an isolation valve, a controller, and three manifolds. The first and second output ports provide pressurized gas to power a vitrector. The output valve alternately provides pressurized gas to the first and second output ports. The isolation valve provides pressurized gas to the output valve. The output valve is located between the isolation valve and the first and second output ports. The controller controls the operation of the isolation valve and the output valve. Two manifolds fluidly connect the output valve to the first and second output ports. A third manifold fluidly connects the isolation valve to the output valve. When the isolation valve allows pressurized gas to flow to the output valve, the output valve operates at a high rate of speed to alternately provide pressurized gas to the first and second output ports thereby powering the vitrector.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
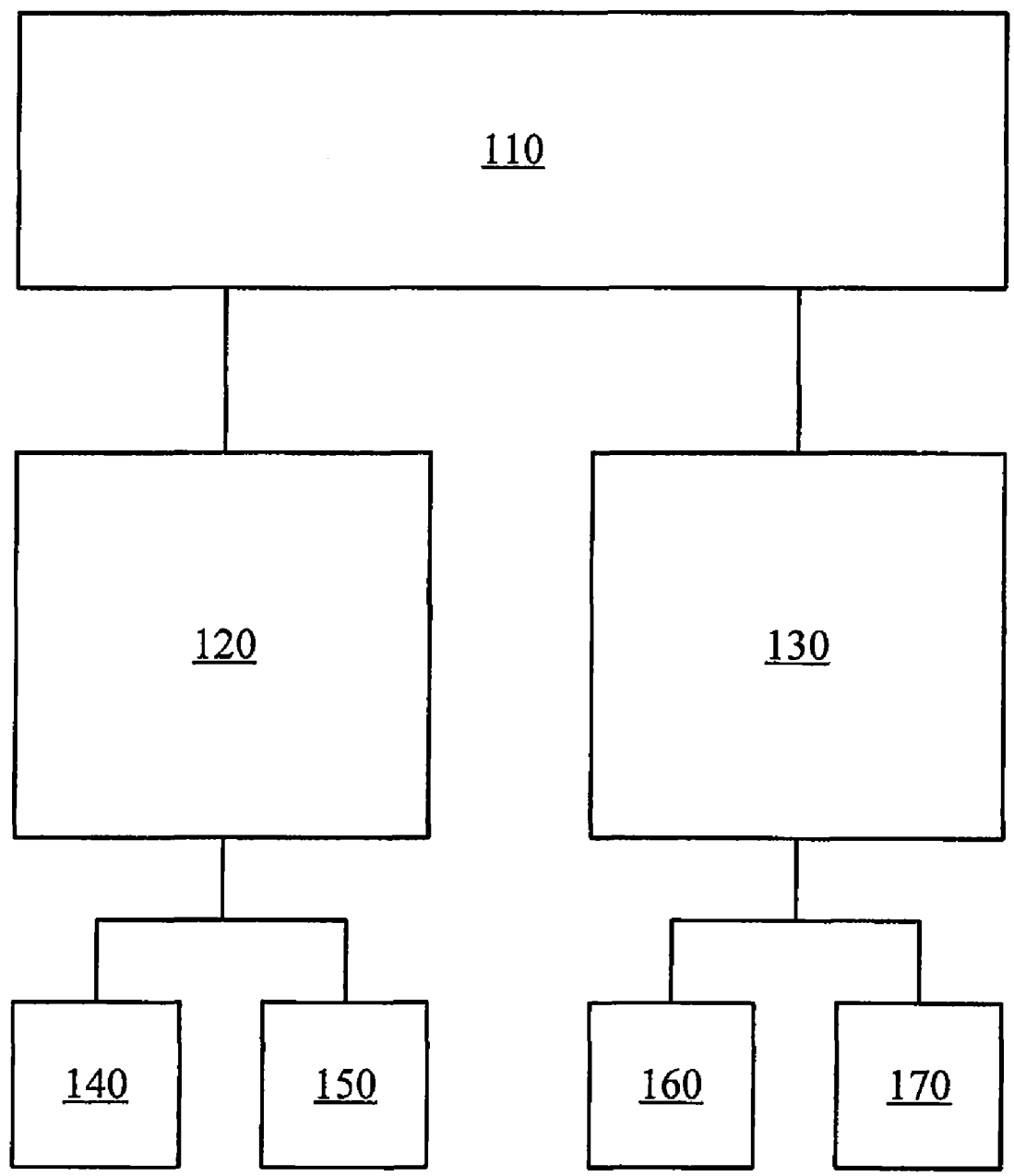
FIG. 1 is a block diagram of a pneumatically-powered ophthalmic surgery machine according to an embodiment of the present invention.

FIG. 1 is a block diagram of a pneumatically powered ophthalmic surgical machine according to an embodiment of the present invention. In FIG. 1, the machine includes gas pressure monitor system 110, proportional controller 120, proportional controller 130, and tools 140, 150, 160, and 170. The tools 140, 150, 160, and 170 can be, for example, scissors, vitrectors, forceps, and injection or extraction modules. Other tools may also be employed with the machine of FIG. 1.

As shown in FIG. 1, gas pressure monitor system 110 is fluidly coupled via a manifold to proportional controllers 120 and 130. A single manifold may connect gas pressure monitor system 110 to proportional controllers 120 and 130, or two separate manifolds may connect gas pressure monitor system 110 to proportional controller 120 and proportional controller 130, respectively.

In operation, the pneumatically powered ophthalmic surgery machine of FIG. 1 operates to assist a surgeon in performing various ophthalmic surgical procedures, such as a vitrectomy. A compressed gas, such as nitrogen, provides the power for tools 140, 150, 160, and 170. The compressed gas passes through gas pressure monitor system 110, through one or more manifolds to proportional controllers 120 and 130, and through additional manifolds and/or tubing to tools 140, 150, 160, and 170.

Gas pressure monitor system 110 functions to monitor the pressure of compressed gas from a gas source as it enters the machine. Proportional controllers 120 and 130 serve to distribute the compressed gas received from gas pressure monitor system 110. Proportional controllers 120 and 130 control the pneumatic power delivered to tools 140, 150, 160, and 170. Various valves, manifolds, and tubing are used to direct compressed gas from gas pressure monitor system 110, through proportional controllers 120 and 130, and to tools 140, 150, 160, and 170. This compressed gas actuates cylinders, for example, in tools 140, 150, 160, and 170.

Figure 2:
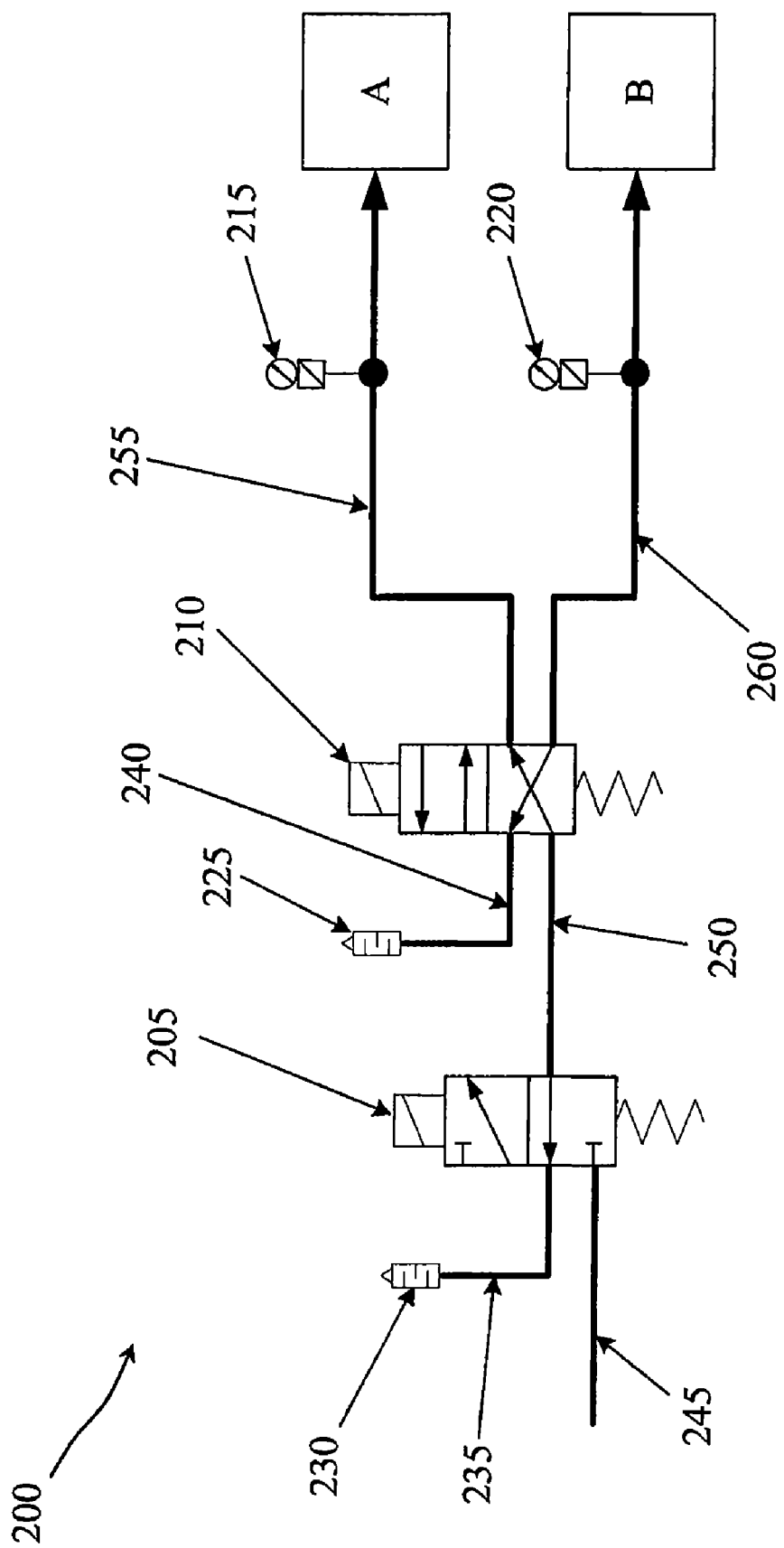
FIG. 2 is a schematic of a pneumatic system for a pneumatically powered vitrectomy machine according to an embodiment of the present invention.

FIG. 2 is a schematic of a pneumatic system for a pneumatically powered vitrectomy machine according to an embodiment of the present invention. In FIG. 2, the pneumatic system includes isolation valve 205, output valve 210, pressure transducers 215 and 220, mufflers 225 and 230, venting manifolds 235 and 240, manifolds 245, 250, 255, and 260, and output ports A and B.

Venting manifold 235 fluidly connects isolation valve 205 to muffler 230. Manifold 245 is also fluidly connected to isolation valve 205. Isolation valve 205 is fluidly connected to output valve 210 by manifold 250. Venting manifold 240 fluidly connects output valve 210 to muffler 225. Manifold 255 fluidly connects output valve 210 to output port A. Manifold 260 fluidly connects output valve 210 to output port B. Pressure transducer 215 is fluidly connected to manifold 255. Likewise, pressure transducer 220 is fluidly connected to manifold 260.

In the embodiment of FIG. 2, isolation valve 205 is a standard two-way valve. As is commonly known, the valve has a solenoid that operates to move the valve to one of the two positions depicted in FIG. 2. As shown, the valve is in a venting position. Pressurized gas can pass from manifold 250, through isolation valve 205, through venting manifold 235, and out of muffler 230. In the other position, isolation valve 205 allows pressurized gas to pass from manifold 245, through isolation valve 205, and into manifold 250 where it can provide power to the vitrector (not shown). Isolation valve 205 is controlled by a controller (not shown).

Output valve 210 is a standard four-way valve. As is commonly known, the valve has a solenoid that operates to move the valve to one of the two positions depicted in FIG. 2. As shown in FIG. 2, the valve is in a position to provide pressurized gas to output port A, and to vent pressurized gas from output port B. In this position, pressurized gas can pass from manifold 250, through output valve 210, through manifold 255, and to output port A where the pressurized gas provides pneumatic power to a vitrector (not shown). Pressurized gas in manifold 260 can pass through output valve 210, venting manifold 240, and muffler 225 where it is exhausted to the atmosphere. In the other position, output valve 210 allows pressurized gas to pass from manifold 250, through output valve 210, through manifold 260, and to output port B where the pressurized gas provides pneumatic power to a vitrector (not shown). Pressurized gas in manifold 255 can pass through output valve 210, venting manifold 240, and muffler 225 where it is exhausted to the atmosphere. Output valve 210 is controlled by a controller (not shown).

The vitrector (not shown) that is attached to output ports A and B acts as a cutting device. The cutter is moved by a cylinder that in turn is moved by pressurized gas. The cylinder oscillates as pressurized gas is alternately directed to output ports A and B. Such a vitrectomy device is designed to operate at about 5,000 cuts per minute.

Pressure transducers 215 and 220 operate to read an atmospheric pressure of the gas contained in manifolds 255 and 260, respectfully. In other words, pressure transducer 215 reads the pressure of the compressed gas that is adjacent to it in manifold 255. Likewise, pressure transducer 220 reads the pressure of the compressed gas that is adjacent to it in manifold 260. In the embodiment of FIG. 2, pressure transducers 215 and 220 are common pressure transducers. Pressure transducers 215 and 220 are capable of reading pressure of a compressed gas and sending an electrical signal containing information about the pressure of the compressed gas to a controller (not shown).

Manifolds 235, 240, 245, 250, 255, and 260 are all configured to carry compressed gas. In the embodiment of FIG. 2, these manifolds are machined out of a metal, such as aluminum. These manifolds are air tight, contain various fittings and couplings, and are designed to withstand relatively high gas pressures. These manifolds may be manufactured as individual pieces or they may be manufactured as a single piece.

For example, manifolds 235, 240, 245, 250, 255, and 260 may be machined from a single piece of aluminum.

Mufflers 225 and 230 are common mufflers designed to suppress the noise made by escaping gas. These mufflers are typically cylindrical in shape.

In operation, pressurized gas is directed alternately to output ports A and B to operate the vitrector. Isolation valve 205 is operated in a position that allows pressurized gas to pass from manifold 245, through isolation valve 205, and into manifold 250. Output valve 210 is alternated between its two positions very rapidly to provide pressurized gas to output ports A and B. In one position, pressurized gas can pass from manifold 250, through output valve 210, through manifold 255, and to output port A where the pressurized gas provides pneumatic power to a vitrector (not shown). Pressurized gas in manifold 260 can pass through output valve 210, venting manifold 240, and muffler 225 where it is exhausted to the atmosphere. In the other position, output valve 210 allows pressurized gas to pass from manifold 250, through output valve 210, through manifold 260, and to output port B where the pressurized gas provides pneumatic power to a vitrector (not shown). Pressurized gas in manifold 255 can pass through output valve 210, venting manifold 240, and muffler 225 where it is exhausted to the atmosphere.

In this manner, pressurized gas is provided to output port A while pressurized gas in manifold 260 is allowed to vent through a venting port to which muffler 225 is attached. Likewise, pressurized gas is provided to output port B while pressurized gas in manifold 255 is allowed to vent through a venting port to which muffler 225 is attached. Due to the quick response of the output valve selected, pressurized gas can be alternated very quickly between manifolds 255 and 260. This allows the vitrector (not shown) to operate at very high cut rates of about 5,000 cuts per minute.

Figure 3:
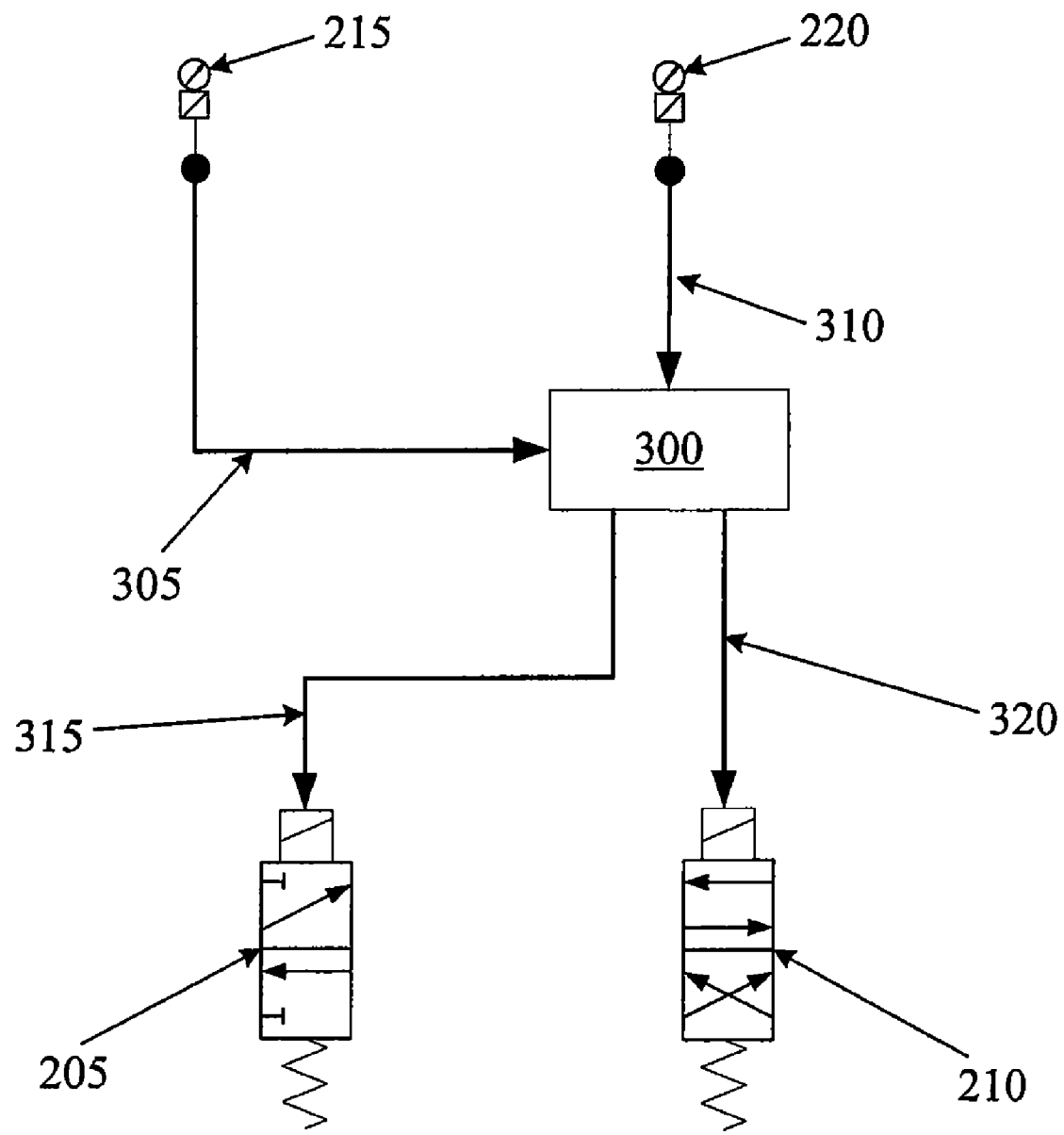
FIG. 3 is a schematic of a controller, valve, and transducer portion of a pneumatic system for a pneumatically powered vitrectomy machine according to an embodiment of the present invention.

FIG. 3 is a schematic of a controller, valve, and transducer portion of a pneumatic system for a pneumatically powered vitrectomy machine according to an embodiment of the present invention. In FIG. 3, controller 300 and interfaces 305, 310, 315, and 320 are depicted along with isolation valve 205, output valve 210, and pressure transducers 215 and 220.

In the embodiment of FIG. 3, controller 300 receives pressure information from pressure transducers 215 and 220 via interfaces 305 and 310, respectively. In this manner, pressure transducer 215 is electrically coupled to controller 300 via interface 305, and pressure transducer 220 is electrically coupled to controller 300 via interface 310. Controller sends control signals to isolation valve 205 and output valve 210 via interfaces 315 and 320, respectively.

Controller 300 is typically an intergraded circuit capable of performing logic functions. In this manner, controller 300 is in the form of a standard integrated circuit package with power, input, and output pins. In various embodiments, controller 300 is a valve controller or a targeted device controller. In such a case, controller 300 performs specific control functions targeted to a specific device, such as a valve. In other embodiments, controller 300 is a microprocessor. In such a case, controller 300 is programmable so that it can function to control valves as well as other components of the machine. In other cases, controller 300 is not a programmable microprocessor, but instead is a special purpose controller configured to control different valves that perform different functions.

Controller 300 is configured to receive signals from pressure transducer 215 via interface 305 and from pressure transducer 220 via interface 310. These signals, for example, correspond to readings of gas pressure in manifolds 255 and 260, respectively. Controller 300 is also configured to send output signals via interfaces 315 and 320 to isolation valve 205 and output valve 210, respectively. These output signals allow controller 300 to control the operation of isolation valve 205 and output valve 210.

Interfaces 305 and 310 are designed to carry signals from pressure transducers 215 and 220 to controller 300. In this case, interfaces 305 and 310 are common electrical conductors such as wires, buses, traces, or the like. Likewise, interfaces 315 and 320 carry signals from controller 300 to isolation valve 205 and output valve 210. Interfaces 305, 310, 315, and 320 may be one or more wires, buses, traces, or the like designed to carry electrical or data signals.

Figure 4:
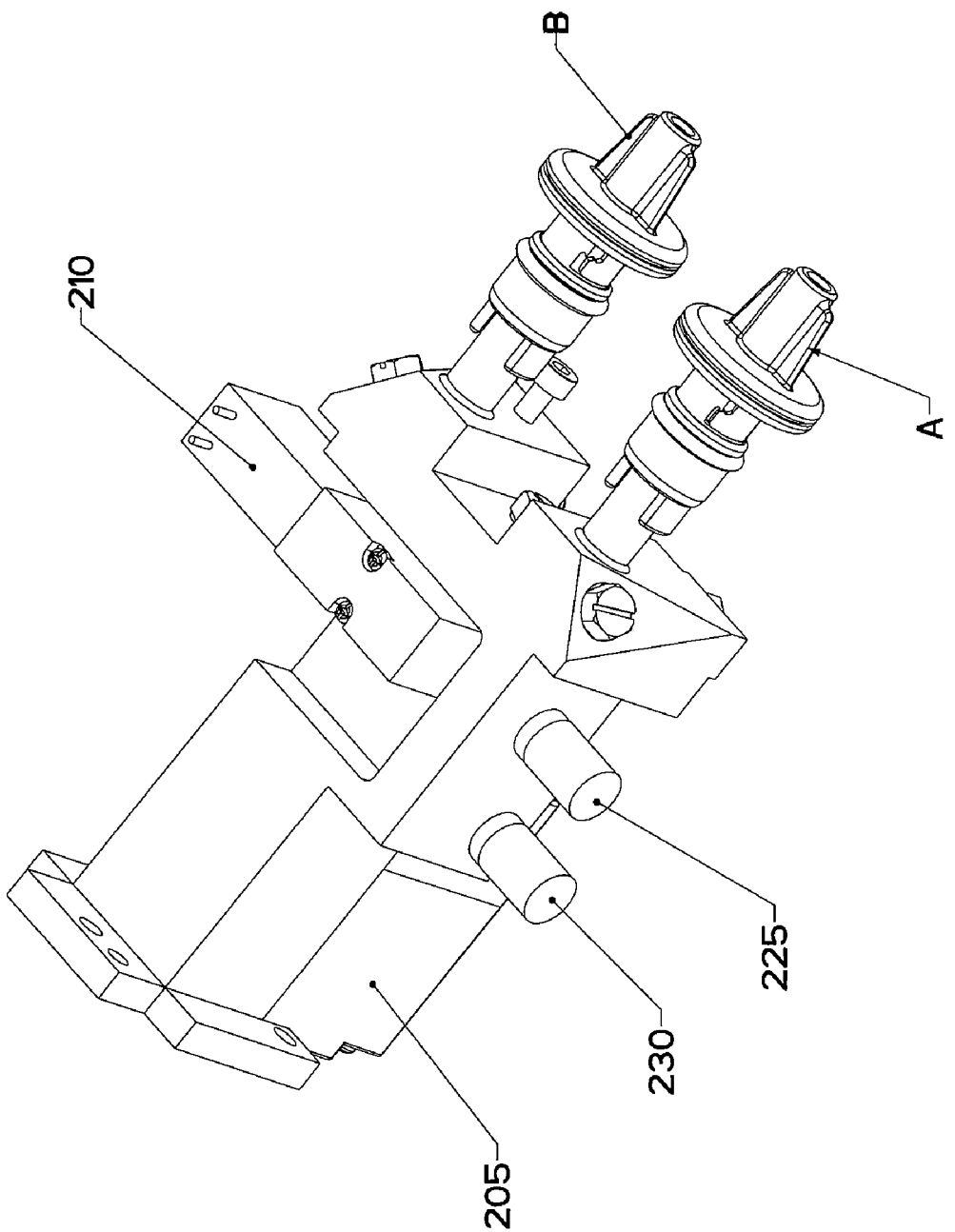
FIG. 4 is a perspective view of a pneumatic system according to an embodiment of the present invention.

FIG. 4 is a perspective view of a pneumatic system according to an embodiment of the present invention. The pneumatic system of FIG. 4 depicts isolation valve 205, output valve 210, mufflers 225 and 230, and output ports A and B. These various components are connected via a series of manifolds machined out of a single piece of aluminum. The characteristics and operation of the pneumatic system of FIG. 4 is similar to that previously described with respect to FIGS. 2 and 3.

Figure 5:
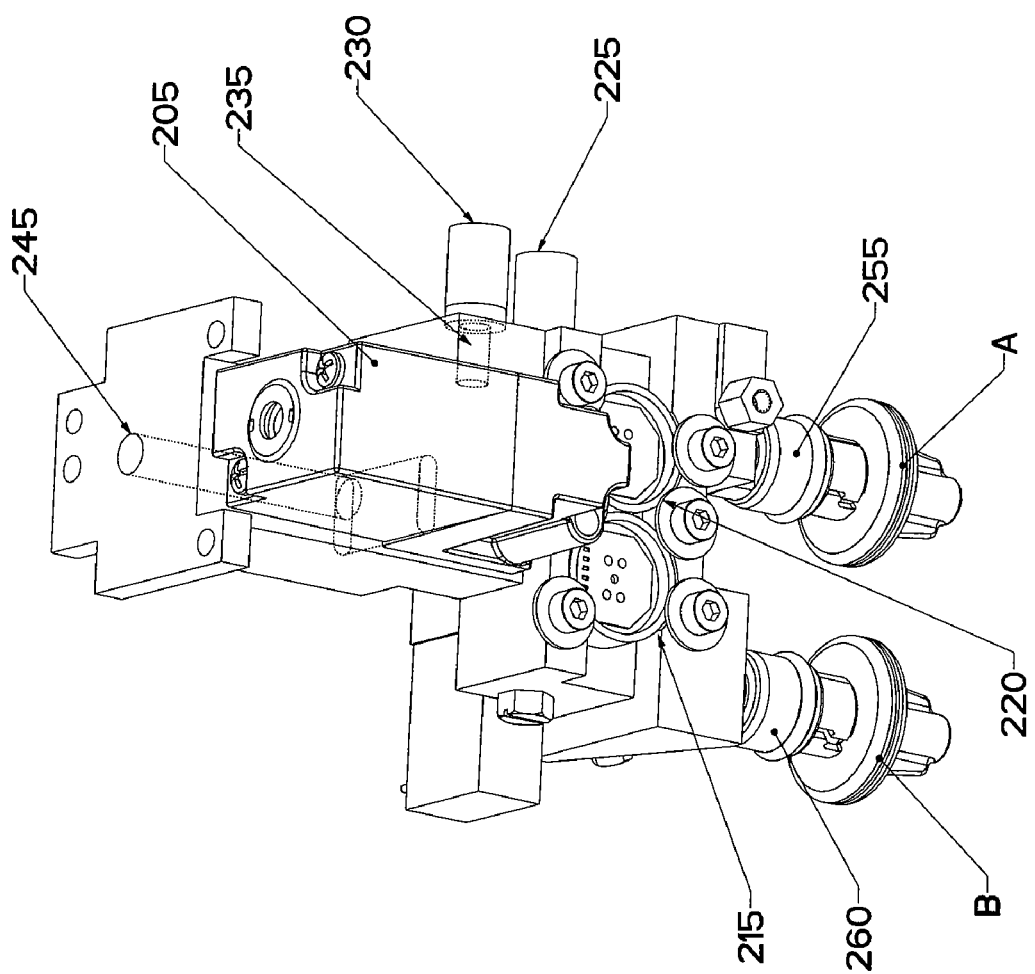
FIG. 5 is a bottom perspective view of a pneumatic system according to an embodiment of the present invention.

FIG. 5 is a bottom perspective view of a pneumatic system according to an embodiment of the present invention. The pneumatic system of FIG. 5 depicts pressure transducers 215 and 220, mufflers 225 and 230, manifolds 235, 245, 255, and 260, and output ports A and B. These various manifolds are machined out of a single piece of aluminum. The characteristics and operation of the pneumatic system of FIG. 5 is similar to that previously described with respect to FIGS. 2 and 3.

Figure 6:
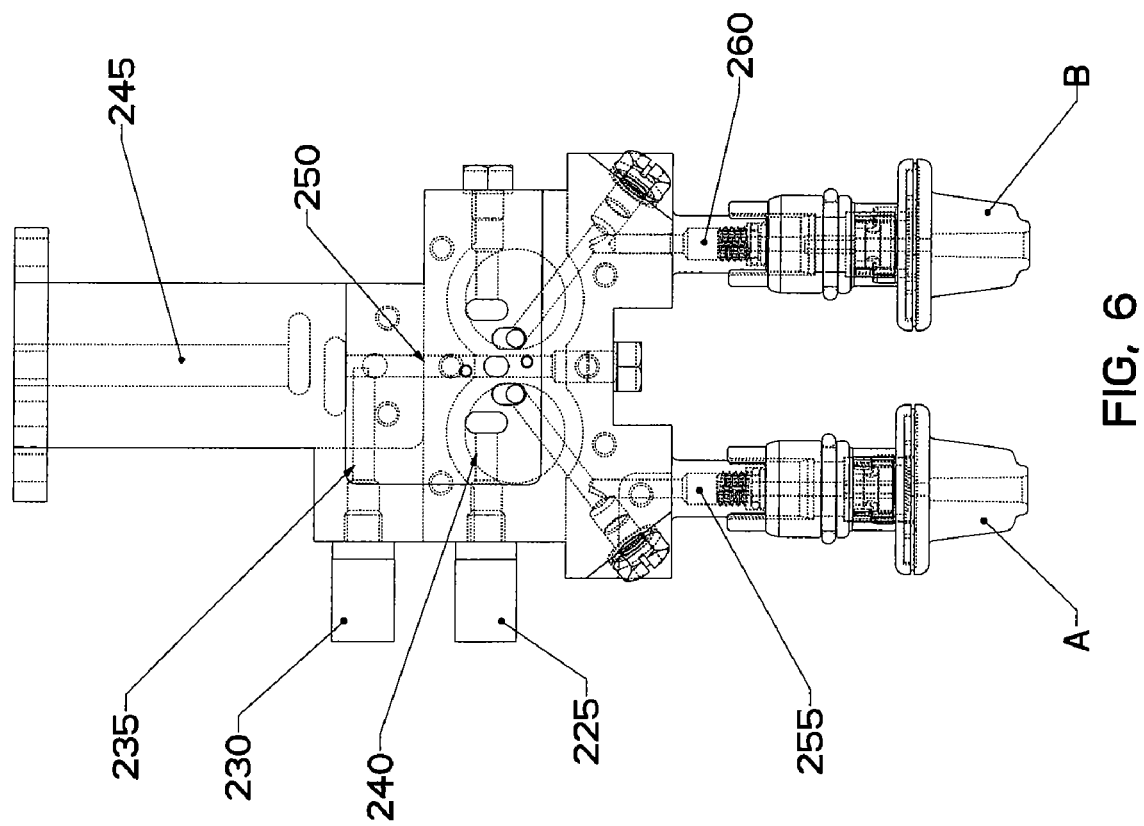
FIG. 6 is a top view of a pneumatic system according to an embodiment of the present invention.

FIG. 6 is a top view of a pneumatic system according to an embodiment of the present invention. The pneumatic system of FIG. 6 depicts mufflers 225 and 230, manifolds 235, 240, 245, 250, 255, and 260, and output ports A and B. These various manifolds are machined out of a single piece of aluminum. The characteristics and operation of the pneumatic system of FIG. 6 is similar to that previously described with respect to FIGS. 2 and 3.

From the above, it may be appreciated that the present invention provides an improved system for providing pneumatic power to a vitrector. The present invention enables the rapid provision of compressed gas to a vitrector with a minimal number of components. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for providing pneumatic power to a vitrector comprising:
    a first output port for providing pressurized gas to a vitrector;
    a second output port for providing pressurized gas to the vitrector;
    an output valve for alternately providing pressurized gas to the first and second output ports;
    an isolation valve for providing pressurized gas to the output valve;
    a first manifold fluidly connecting the output valve to the first output port;
    a second manifold fluidly connecting the output valve to the second output port; and
    a third manifold fluidly connecting the isolation valve to the output valve;

wherein when the isolation valve provides pressurized gas to the output valve, the output valve operates at a high rate of speed to alternately provide pressurized gas to the first and second output ports thereby powering the vitrector.

2. The system of claim 1 further comprising:
a first venting port fluidly connected to the isolation valve via a first venting manifold; and
a second venting port fluidly connected to the output valve via a second venting manifold.

3. The system of claim 2 further comprising:
a first muffler connected to the first venting port; and
a second muffler connected to the second venting port.

4. The system of claim 1 further comprising:
a pressure transducer located near the output valve.

5. The system of claim 1 further comprising:
a pressure transducer located between the output valve and the first output port.

6. The system of claim 1 wherein the output valve is located between the isolation valve and the first output port.

7. The system of claim 1 wherein the output valve is a four-way valve and the isolation valve is a two-way valve.

8. The system of claim 1 further comprising:
a controller adapted to operate the output valve and the isolation valve.

9. The system of claim 8 wherein the controller further receives information from a pressure transducer.

10. The system of claim 1 wherein the output valve is operated to cause the vitrector to operate at about 5,000 cuts per minute.

11. A system for providing pneumatic power to a vitrector comprising:
a first output port for providing pressurized gas to a vitrector;
a second output port for providing pressurized gas to the vitrector;
an isolation valve for controlling the flow of pressurized gas to an output valve, the output valve for alternately providing pressurized gas to the first and second output ports, the output valve located between the isolation valve and the first and second output ports;
a controller for controlling the operation of the isolation valve and the output valve;
a first manifold fluidly connecting the output valve to the first output port;
a second manifold fluidly connecting the output valve to the second output port; and
a third manifold fluidly connecting the isolation valve to the output valve;
wherein when the isolation valve allows pressurized gas to flow to the output valve, the output valve operates at a high rate of speed to alternately provide pressurized gas to the first and second output ports thereby powering the vitrector.

12. The system of claim 11 further comprising:
a first venting port fluidly connected to the isolation valve via a first venting manifold; and
a second venting port fluidly connected to the output valve via a second venting manifold.

13. The system of claim 12 further comprising:
a first muffler connected to the first venting port; and
a second muffler connected to the second venting port.

14. The system of claim 11 further comprising:
a pressure transducer located near the output valve.

15. The system of claim 11 further comprising:
a pressure transducer located between the output valve and the first output port.

16. The system of claim 11 wherein the output valve is a four-way valve and the isolation valve is, a two-way valve.

17. The system of claim 11 wherein the controller further receives information from a pressure transducer.

18. The system of claim 11 wherein the controller operates the output valve to cause the vitrector to operate at about 5,000 cuts per minute.

* * * * *